US008743358B2

(12) United States Patent
Treado et al.

(10) Patent No.: US 8,743,358 B2
(45) Date of Patent: Jun. 3, 2014

(54) SYSTEM AND METHOD FOR SAFER DETECTION OF UNKNOWN MATERIALS USING DUAL POLARIZED HYPERSPECTRAL IMAGING AND RAMAN SPECTROSCOPY

(71) Applicant: ChemImage Corporation, Pittsburgh, PA (US)

(72) Inventors: Patrick Treado, Pittsburgh, PA (US); Matthew Nelson, Harrison City, PA (US); Charles Gardner, Gibsonia, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

(21) Appl. No.: 13/842,098

(22) Filed: Mar. 15, 2013

(65) Prior Publication Data
US 2014/0118722 A1 May 1, 2014

Related U.S. Application Data

(63) Continuation-in-part of application No. 13/651,600, filed on Oct. 15, 2012, and a continuation-in-part of application No. 13/373,333, filed on Nov. 10, 2011.

(51) Int. Cl.
G01J 3/28 (2006.01)
(52) U.S. Cl.
USPC ........................................................ 356/326
(58) Field of Classification Search
USPC .............................. 356/72–73, 301, 326, 328
See application file for complete search history.

(56) References Cited

U.S. PATENT DOCUMENTS 3,398,294 A 8/1968 Groschwitz
4,560,275 A 12/1985 Goetz
5,196,682 A 3/1993 Englehardt
5,216,484 A 6/1993 Chao et al.
(Continued)

FOREIGN PATENT DOCUMENTS

EP 17646438 1/2007
EP 1902301 3/2008
(Continued)

OTHER PUBLICATIONS

Sharma, et al, "Stand-Off Raman Spectroscopic Detection of Minerals on Planetary Surfaces", Hawaii Institute of Geophysics and Planetology, pp. 2391-2407, 2003.
(Continued)

Primary Examiner — Tarifur Chowdhury
Assistant Examiner — Abdullahi Nur
(74) Attorney, Agent, or Firm — Pepper Hamilton LLP

(57) ABSTRACT

A first location comprising an unknown material may be scanned using SWIR hyperspectral imaging in a dual polarization configuration. Surveying may also be applied to thereby determine whether or not a human is present. This surveying may be achieved my assessing LWIR data, data acquired from motion sensors, and combinations thereof. If no human is present, a second location may be interrogated using Raman spectroscopic techniques to thereby obtain a Raman data set representative of the region of interest. This Raman data set may be assessed to associate an unknown material with a known material. This assessment may be achieved by comparing the Raman data set to one or more reference data sets in a reference database, where each reference data set is associated with a known material.

36 Claims, 14 Drawing Sheets

(56) References Cited

U.S. PATENT DOCUMENTS

| | | |
|---|---|---|
| 5,394,237 A | 2/1995 | Chang |
| 6,006,140 A | 12/1999 | Carter |
| 6,244,535 B1 | 6/2001 | Felix |
| 6,274,871 B1 | 8/2001 | Dukor et al. |
| 6,422,508 B1 | 7/2002 | Barnes |
| 6,477,907 B1 | 11/2002 | Chambers |
| 6,606,566 B1 | 8/2003 | Sunshine |
| 6,658,915 B2 | 12/2003 | Sunshine |
| 6,820,012 B2 | 11/2004 | Sunshine |
| 6,822,742 B1 | 11/2004 | Kalayeh |
| 6,844,817 B2 | 1/2005 | Gleine |
| 6,967,612 B1 | 11/2005 | Gorman |
| 6,985,216 B2 | 1/2006 | Treado |
| 6,985,233 B2 | 1/2006 | Tuschel |
| 6,995,371 B2 | 2/2006 | Garber |
| 6,995,846 B2 | 2/2006 | Kalayeh |
| 7,012,695 B2 | 3/2006 | Maier |
| 7,084,972 B2 | 8/2006 | Treado |
| 7,088,435 B2 | 8/2006 | Brestel et al. |
| 7,164,117 B2 | 1/2007 | Breed |
| 7,193,210 B2 | 3/2007 | Garber |
| 7,239,974 B2 | 7/2007 | Gulati |
| 7,246,613 B1 | 7/2007 | Mohar |
| 7,262,839 B2 | 8/2007 | Treado |
| 7,277,178 B2 | 10/2007 | Shpantzer |
| 7,286,222 B2 * | 10/2007 | Gardner, Jr. ........... 356/301 |
| 7,295,308 B1 | 11/2007 | Samuels |
| 7,307,705 B2 | 12/2007 | Treado |
| 7,322,267 B1 | 1/2008 | Munson |
| 7,386,372 B2 | 6/2008 | Breed |
| 7,417,727 B2 | 8/2008 | Polonskiy |
| 7,420,664 B2 | 9/2008 | Treado et al. |
| 7,420,675 B2 | 9/2008 | Giakos |
| 7,440,096 B2 | 10/2008 | Gardner |
| 7,486,395 B2 | 2/2009 | Treado |
| 7,502,118 B2 | 3/2009 | Shpantzer |
| 7,511,624 B2 | 3/2009 | Shaw |
| 7,525,102 B1 | 4/2009 | Henshaw |
| 7,541,588 B2 | 6/2009 | Tabirian |
| 7,542,138 B2 | 6/2009 | Gardner |
| 7,548,310 B2 | 6/2009 | Gardner |
| 7,551,715 B2 | 6/2009 | Rothschild |
| 7,573,570 B2 | 8/2009 | Zhang |
| 7,596,242 B2 | 9/2009 | Breed |
| 7,644,606 B2 | 1/2010 | Sheen |
| 7,663,502 B2 | 2/2010 | Breed |
| 7,676,062 B2 | 3/2010 | Breed |
| 7,687,276 B2 | 3/2010 | Kunz |
| 7,692,775 B2 | 4/2010 | Treado et al. |
| 8,379,193 B2 | 2/2013 | Gardner |
| 2001/0052979 A1 | 12/2001 | Treado et al. |
| 2003/0058112 A1 | 3/2003 | Gleine |
| 2003/0123056 A1 | 7/2003 | Barnes |
| 2003/0216869 A1 | 11/2003 | Sunshine |
| 2004/0051867 A1 | 3/2004 | Brestel |
| 2004/0191859 A1 | 9/2004 | Tabacco |
| 2004/0253759 A1 | 12/2004 | Garber |
| 2005/0030533 A1 | 2/2005 | Treado |
| 2005/0030545 A1 | 2/2005 | Tuschel |
| 2005/0030657 A1 | 2/2005 | Maier |
| 2005/0041244 A1 | 2/2005 | Treado |
| 2005/0079626 A1 | 4/2005 | Kunz |
| 2005/0105099 A1 | 5/2005 | Shpantzer |
| 2005/0134859 A1 | 6/2005 | Kalayeh |
| 2005/0264813 A1 | 12/2005 | Giakos |
| 2006/0007437 A1 | 1/2006 | Treado |
| 2006/0021498 A1 | 2/2006 | Moroz |
| 2006/0022139 A1 | 2/2006 | Garber |
| 2006/0146315 A1 | 7/2006 | Treado |
| 2006/0167595 A1 | 7/2006 | Breed et al. |
| 2006/0170922 A1 | 8/2006 | Wang et al. |
| 2006/0203238 A1 | 9/2006 | Gardner, Jr. et al. |
| 2006/0208169 A1 | 9/2006 | Breed et al. |
| 2006/0209301 A1 | 9/2006 | Gardner, Jr. et al. |
| 2006/0254522 A1 | 11/2006 | Shaw |
| 2006/0256330 A1 | 11/2006 | Leipertz |
| 2006/0262304 A1 | 11/2006 | Carron |
| 2006/0268266 A1 | 11/2006 | Gardner |
| 2007/0007384 A1 | 1/2007 | Sliwa |
| 2007/0081156 A1 | 4/2007 | Treado |
| 2007/0086624 A1 | 4/2007 | Breed |
| 2007/0098142 A1 | 5/2007 | Rothschild |
| 2007/0118324 A1 | 5/2007 | Gulati |
| 2007/0125951 A1 | 6/2007 | Snider |
| 2007/0127030 A1 | 6/2007 | Shpantzer |
| 2007/0153268 A1 | 7/2007 | Panza et al. |
| 2007/0163431 A1 | 7/2007 | Mohar |
| 2007/0216898 A1 | 9/2007 | Gardner |
| 2007/0221849 A1 | 9/2007 | Tabirian |
| 2007/0262574 A1 | 11/2007 | Breed |
| 2007/0268485 A1 | 11/2007 | Polonskiy |
| 2007/0282506 A1 | 12/2007 | Breed |
| 2008/0036580 A1 | 2/2008 | Breed |
| 2008/0036593 A1 | 2/2008 | Rose-Pehrsson |
| 2008/0051957 A1 | 2/2008 | Breed |
| 2008/0084560 A1 | 4/2008 | Zhang |
| 2008/0088837 A1 | 4/2008 | Gardner |
| 2008/0129581 A1 | 6/2008 | Douglass |
| 2008/0144885 A1 | 6/2008 | Zucherman |
| 2008/0154535 A1 | 6/2008 | Sparks |
| 2008/0157940 A1 | 7/2008 | Breed |
| 2008/0165344 A1 | 7/2008 | Treado |
| 2008/0180675 A1 | 7/2008 | Sheen |
| 2008/0191137 A1 | 8/2008 | Poteet |
| 2008/0198365 A1 | 8/2008 | Treado |
| 2008/0204757 A1 | 8/2008 | Manning |
| 2008/0236275 A1 | 10/2008 | Breed |
| 2008/0258071 A1 | 10/2008 | Arnold |
| 2008/0268548 A1 | 10/2008 | Zuckerman |
| 2008/0295783 A1 | 12/2008 | Furton |
| 2009/0046538 A1 | 2/2009 | Breed |
| 2009/0092284 A1 | 4/2009 | Breed |
| 2009/0095885 A1 | 4/2009 | Hager |
| 2009/0101843 A1 | 4/2009 | Henshaw |
| 2009/0128802 A1 | 5/2009 | Treado et al. |
| 2009/0202128 A1 | 8/2009 | Gorian et al. |
| 2009/0236528 A1 | 9/2009 | Shpantzer |
| 2009/0252650 A1 | 10/2009 | Lakshmanan |
| 2009/0257555 A1 | 10/2009 | Chalmers |
| 2009/0322485 A1 | 12/2009 | Barnes |
| 2010/0225899 A1 | 9/2010 | Treado |
| 2011/0033082 A1 | 2/2011 | Beckstead |
| 2011/0080577 A1 | 4/2011 | Nelson |
| 2011/0085164 A1 | 4/2011 | Nelson |
| 2011/0089323 A1 | 4/2011 | Treado |

FOREIGN PATENT DOCUMENTS

| | | |
|---|---|---|
| EP | 2083259 | 7/2009 |
| WO | WO/91/08466 | 6/1991 |
| WO | WO/01/33212 | 5/2001 |
| WO | WO0140896 | 6/2001 |
| WO | WO/03/059735 | 7/2003 |
| WO | WO/03/102534 | 11/2003 |
| WO | WO/2005/008198 | 1/2005 |
| WO | WO2005001900 | 1/2005 |
| WO | WO/2005008200 | 1/2005 |
| WO | WO/2005/010474 | 3/2005 |
| WO | WO/2007/001379 | 1/2007 |
| WO | WO/2007/011391 | 1/2007 |
| WO | WO/2007/013000 | 2/2007 |
| WO | WO/2007/032814 | 3/2007 |
| WO | WO/2007/044067 | 4/2007 |
| WO | WO/2007/044593 | 4/2007 |
| WO | WO/2007/051092 | 5/2007 |
| WO | WO/2007/056753 | 5/2007 |
| WO | WO/2007/084099 | 7/2007 |
| WO | WO/2007/101297 | 9/2007 |
| WO | WO/2007/120996 | 10/2007 |
| WO | PCT/US06/22647 | 11/2007 |
| WO | WO/2007/103897 | 11/2007 |
| WO | WO/2007/123555 | 11/2007 |
| WO | WO/2008/002659 | 1/2008 |
| WO | WO/2008/010832 | 1/2008 |

(56) References Cited

FOREIGN PATENT DOCUMENTS

| WO | WO/2008/097262 | 3/2008 |
|----|----|----|
| WO | WO/2008/048979 | 4/2008 |
| WO | WO/2008/024344 | 6/2008 |
| WO | WO/2008/105812 | 9/2008 |
| WO | WO/2008/140473 | 11/2008 |
| WO | WO2009019689 | 2/2009 |
| WO | WO2009154765 | 12/2009 |
| WO | WO2010108086 | 9/2010 |

OTHER PUBLICATIONS

Sharma, et al, Portable Stand-off Raman and Mie-Rayleigh LIDAR for Cloud, Aerosols, and Chemical Monitoring, Proceedings of SPIE vol. 5154, LIDAR Remote Sensing for Environmental Monitoring IV, pp. 1-14, 2003.

Sharma, et al., Remote Pulsed Laser Raman Spectroscopy System for Mineral Analysis on Planetary Surfaces to 66 Meters, Applied Spectroscopy, vol. 56, No. 6, 2002, pp. 699-705.

PCT/US06/22647, Notification of Transmittal of the International Search Report and the Written Opinion of the International Searching Authority, Mar. 31, 2008.

Gardner, C. et al, "Remote Chemical Biological and Explosive Agent Detection Using a Robot-Based Raman Detector". SPIE Defense+Security, Proc. SPIE 6962, 69620T (2008).

Pati, B et al., "Passively Q-switched Nd:YLF laser in a D-rod configuration," in Conference on Lasers and Electro-Optics, OSA Technical Digest (Optical Society of America, Washington, DC 2008), paper CFJ5.

Fuller, M. et al., "High gain end pumped lasers," OSA TOPS, vol. 19, Advanced Solid State Lasers, Walter Bosenberg and Martin M. Feijer (eds), 1998, Optical Society of America.

Kyusho, Y et al., "High-energy subnanosecond compact laser system with diode-pumped, Q-switched Nd:YVO4 laser," OSA Tops on Advanced Solid State Lasers, vol. 1, Stephen A. Payne and Clifford Pollock (eds), 1996, Optical Society of America.

Zheng, S. et al, "Laser-diode end-pumped passively Q-switched laser with Cr4+:YAG saturable absorber," Opt. Engineering, vol. 41, # 9, 2002, pp. 2271-2275.

Nelson et al, "Single-Shot Multiwavelength Imaging of Laser Plumes," Applied Spectroscopy, vol. 52, No. 2, Feb. 1, 1998.

Extended European Search Report, PCT/US2006022647. Aug. 10, 2010.

* cited by examiner

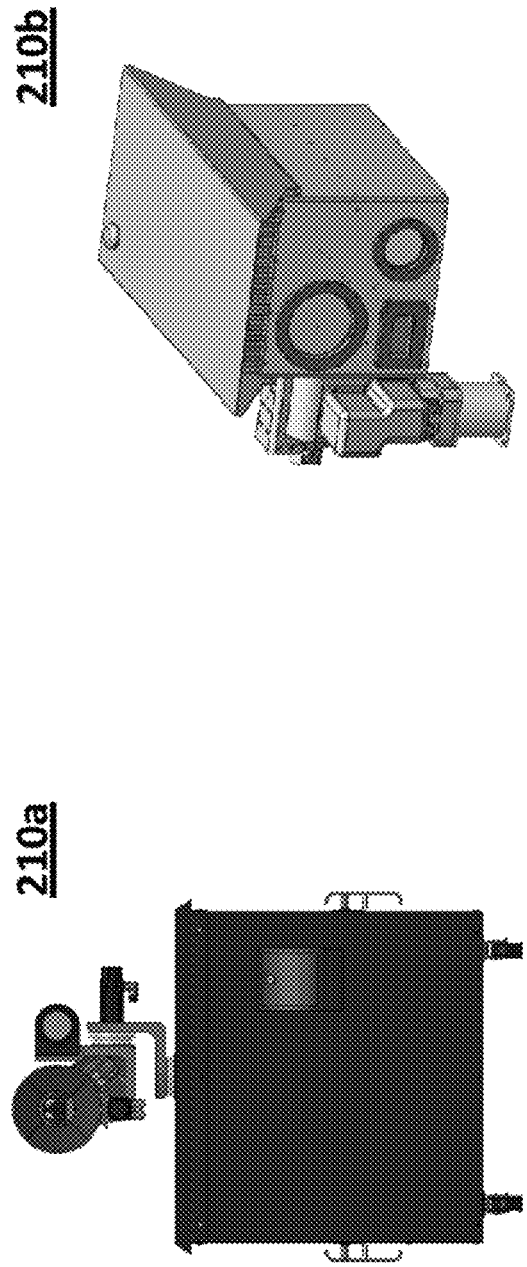

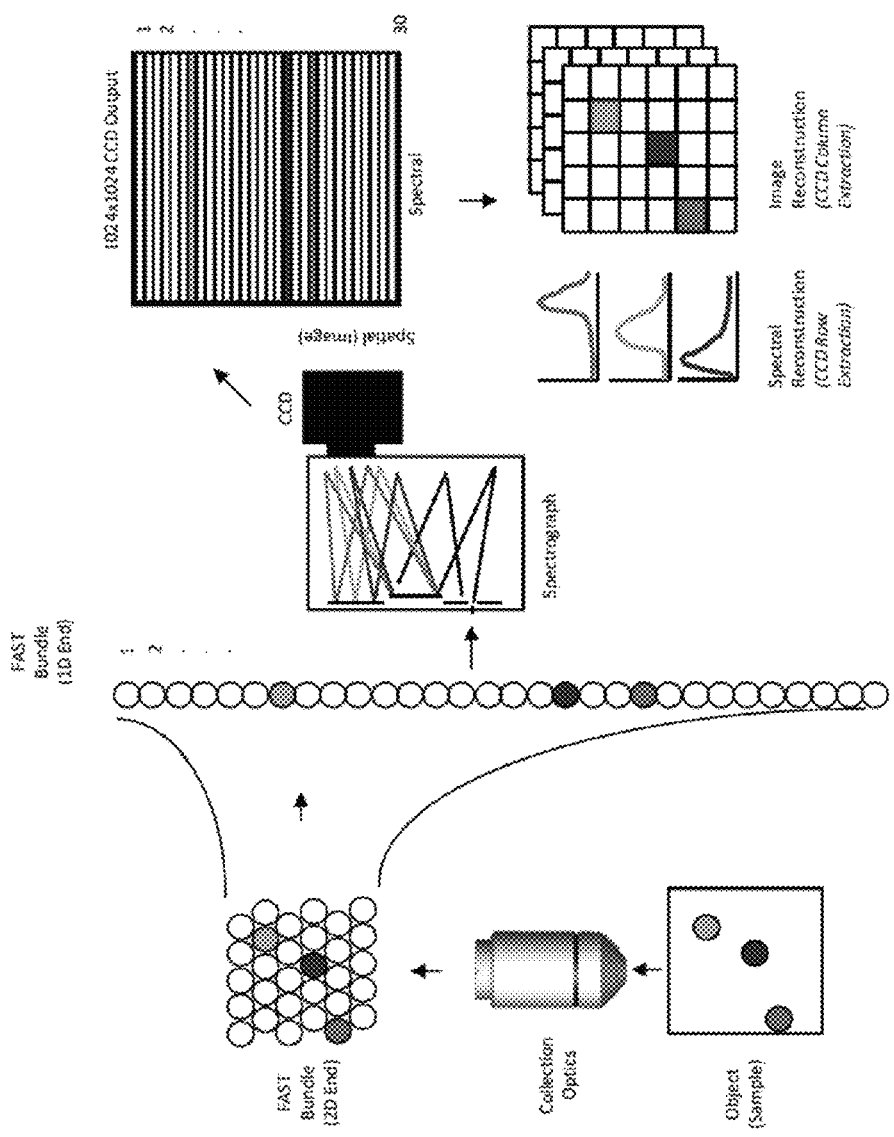
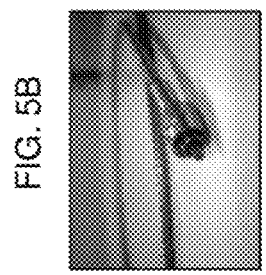
FIG. 5A
FIG. 5B

SYSTEM AND METHOD FOR SAFER DETECTION OF UNKNOWN MATERIALS USING DUAL POLARIZED HYPERSPECTRAL IMAGING AND RAMAN SPECTROSCOPY

RELATED APPLICATIONS

This application is a continuation-in-part to pending U.S. patent application Ser. No. 13/842,098, filed on Mar. 15, 2013, entitled "System and Method for Safer Detection of Unknown Materials Using Dual Polarized Hyperspectral Imaging and Raman Spectroscopy," which itself claims priority to Ser. No. 13/651,600, filed on Oct. 15, 2012, entitled "Dual Polarization with Liquid Crystal Tunable Filters" and U.S. patent application Ser. No. 13/373,333, filed on Nov. 10, 2011, entitled "System and Method for Eye Safe Detection of Unknown Targets." These applications are hereby incorporated by reference in their entireties.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger targets, in the range of millimeter to meter dimensions, macro lens optics is appropriate. For samples located within relatively inaccessible environments, flexible fiberscope or rigid borescopes can be employed. For very large scale targets, such as planetary targets, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the entire area encompassing the sample simultaneously using an electronically tunable optical imaging filter such as an acousto-optic tunable filter (AOTF) or a LCTF. This may be referred to as "wide-field imaging". Here, the organic material in such optical filters is actively aligned by applied voltages to produce the desired bandpass and transmission function. The spectra obtained for each pixel of such an image thereby forms a complex data set referred to as a hyperspectral image (HSI) which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet (UV), visible (VIS), near infrared (NIR), short-wave infrared (SWIR), mid infrared (MIR), long wave infrared (LWIR) wavelengths and to some overlapping ranges. These correspond to wavelengths of about 180-380 nm (UV), 380-700 nm (VIS), 700-2500 nm (NIR), 850-1800 nm (SWIR), 2500-25000 nm (MIR), and 7500-13500 nm (LWIR).

Proliferation of chemical, biological, and explosive (CBE) threats is a growing danger to civilian and military personnel. There exists a need for sensor systems that can rapidly detect these CBE threats at a standoff distance. It would be advantageous of the system could also detect other materials such as hazardous and non-hazardous materials and drugs (both illegal and pharmaceuticals). Examples of technologies that hold potential for such detection include short wave infrared (SWIR) spectroscopy and Raman spectroscopy.

Raman spectroscopy requires probing a sample with a laser beam. The issue of laser safety must be addressed before widespread deployment is possible. There exists a need to develop strategies to reduce the laser hazard to both operators and bystanders.

There also exists a need to increase speed of detection and analysis of unknown materials. A LCTF uses birefringent retarders to distribute the light energy of an input light signal over a range of polarization states. The polarization state of light emerging at the output of the LCTF is caused to vary as a function of wavelength due to differential retardation of orthogonal components of the light, contributed by the birefringent retarders. The LCTF discriminates for wavelength-specific polarization using a polarizing filter at the output. The polarizing filter passes the light components in the output that are rotationally aligned to the polarizing filter. The LCTF is tuned by adjusting the birefringence of the retarders so that a specific discrimination wavelength emerges in a plane polarized state, aligned to the output polarizing filter. Other wavelengths that emerge in other polarization states and/or alignments are attenuated.

A highly discriminating spectral filter is possible using a sequence of several birefringent retarders. The thicknesses, birefringences, and relative rotation angles of the retarders are chosen to correspond to the discrimination wavelength. More specifically, the input light signal to the filter becomes separated into orthogonal vector components, parallel to the respective ordinary and extraordinary axes of each birefringent retarder when encountered along the light transmission path through the filter. These separated vector components are differentially retarded due to the birefringence; such differential retardation also amounts to a change in their polarization state. For a plane polarized component at the input to the filter, having a specific rotational alignment at the input to the filter and at specific discrimination wavelengths, the light components that have been divided and subdivided all emerge from the filter in the same polarization state and alignment, namely plane polarized and in alignment with the selection polarizer (i.e., the polarizing filter) at the output.

A filter as described is sometimes termed an interference filter because the components that have been divided and subdivided from the input and interfere positively at the output selection polarizer are the components that are passed. Such filters also are sometimes described with respect to a rotational twist in the plane polarization alignment of the discriminated component between the input and the selection polarizer at the output.

There are several known configurations of spectral filters comprising birefringent retarders, such as the Lyot, Solc and Evans types. Such filters can be constructed with fixed (non-tunable) birefringent crystals for the retarders. A filter with retarders that are tuned in unison permits adjustment of the bandpass wavelength. Tunable retarders can comprise liquid crystals or composite retarder elements each comprising a fixed crystal and an optically aligned liquid crystal.

The thicknesses, birefringences, and rotation angles of the retarders are coordinated such that each retarder contributes part of the necessary change in polarization state to alter the polarization state of the passband wavelength from an input reference angle to an output reference angle. The input reference angle may be, for example, 45° to the ordinary and extraordinary axes of a first retarder in the filter. The output reference angle is the rotational alignment of the polarizing filter (or "selection polarizer").

A spectral filter may have a comb-shaped transmission characteristic. Increasing or decreasing the birefringence when tuning to select the discrimination wavelength (or passband), stretches or compresses the comb shape of the transmission characteristic along the wavelength coordinate axis.

If the input light is randomly polarized, the portion that is spectrally filtered is limited to the vector components of the input wavelengths that are parallel to one of the two orthogonal polarization components that are present. Only light at the specific wavelength, and at a given reference polarization alignment at the input, can emerge with a polarization angle aligned to the rotational alignment of the selection polarizer at the output. The light energy that is orthogonal to the reference alignment at the input, including light at the passband wavelength, is substantially blocked.

A LCTF thus passes only one of two orthogonal components of input light. The transmission ratio in the passband is at a maximum for incident light at the input to the LCTF that is aligned to a reference angle of the LCTF. Transmission is at minimum for incident light energy at the input is orthogonal to that reference angle. If the input light in the passband is randomly polarized, the best possible transmission ratio in the passband is fifty percent. It is therefore desirable to devise a system and method wherein both orthogonal components of the input light are allowed to transmit through the tunable filter, thereby effectively doubling the throughput at the filter output.

SUMMARY

The present disclosure relates generally to a system and method for assessing unknown materials. More specifically, the present disclosure provides for a system and method for detecting and identifying unknown materials using SWIR and Raman spectroscopic techniques. Areas of interest, likely to comprise CBE threats, hazardous agents, and/or drug materials may be targeted during wide area surveillance of a sample scene using SWIR techniques. This disclosure provides for local confirmation of these materials using standoff detection via a Raman-ST sensor. This disclosure also provides for systems and methods that may reduce safety risks associated with operating a laser, which may be enabled by surveying an area using motion detectors and LWIR data.

Hyperspectral sensors hold potential for the detection of unknown materials. The present disclosure provides for a Raman standoff (Raman-ST) sensor which may incorporate fiber array spectral translator (FAST) hyperspectral imaging technology. A FAST device provides for collecting Raman scattered photons from a scene through a telescope (or other lens assembly) and project them onto the two dimensional end of a FAST bundle that is drawn into a one dimensional, distal array coupled to an imaging spectrograph. Software may then extract the full spectral/spatial information, which is embedded in a single CCD image frame. The acquired spatial-specific Raman information allows materials to be computationally differentiated within a complex mixture of background materials.

Raman hyperspectral technology holds potential for the standoff detection of unknown materials and provides for: highly selective detection combined with spatially-independent sampling benefits. LWIR detection techniques and human object imaging and tracking algorithms, used in conjunction with Raman HSI hold potential for reducing safety risks associated with operating a laser. If a human is detected in a scene, a shutter may be configured to prevent subsequent illumination by the laser. The present disclosure also contemplates that mid wave infrared (MWIR) may be used either alone or in conjunction with another spectroscopic technique such as Raman, SWIR, LWIR, visible, and combinations thereof.

The present disclosure also provides for hyperspectral imaging using techniques for dual beam processing through a plurality of tunable filters, including processing both orthogonal polarization components of the incident light at the input to the tunable filters. The configuration provided herein overcomes the limitations of the prior art by maximizing the light transmission ratio during spectrally filtered imaging using the tunable filters. This configuration also holds potential for increasing speed of detection and analysis.

The present disclosure relates to a method for spectral imaging using two tunable filters sensitive to a polarization orientation of a light input beam from an objective lens, wherein the light input beam is to be spectrally filtered by the two tunable filters and coupled to at least one imaging lens. The method comprises: splitting the light input beam into a first and a second beams with respectively orthogonal polarization components; applying the first beam to a first one of the two tunable filters and the second beam to a second one of the two tunable filters such that a polarization component in each of the first and the second beams is filtered by a respective tunable filters to transmit a corresponding passband wavelength; and arranging the imaging lens relative to filtered first and second beams at respective outputs of the two tunable filters so as to focus images from both of the filtered first and second beams. The present disclosure contemplates that the filtered beams may be displayed in either an overlaid or non-overlaid configuration. The present disclosure also contemplates that the beams may be displayed on a single detector or more than one detector.

It is an aspect of the disclosure that these techniques can be accomplished in a way that facilitates use of the tunable filters in imaging applications. In that case, the two tunable filters can be oriented orthogonally relative to one another, and disposed to form an image through the same optics. The input light is split into its orthogonal plane polarized beams and each beam is aligned to the reference angle of one of the tunable filters. The resulting cross-polarized images are either overlaid on one another or displayed in a non-overlaid configuration.

In this embodiment, it is possible to tune the two adjacent tunable filters to the same passband, thereby maximizing the intensity of the passband at the photodetector array. Alternatively, the two adjacent tunable filters can be tuned to different passband wavelengths. In a case where a given material or object of interest is characterized by two wavelength peaks, simultaneously displaying the images at two distinct wavelengths on one or more detectors holds potential for increasing the speed of detection. For example, if two images are displayed simultaneously for a material or object characterized by two wavelength peaks, then the speed of detection becomes the frame rate of the camera. Such a configuration holds potential for detection in real time. In other embodiments where a material or object is characterized by n-number of wavelength peaks, then detection can be achieved in a shorter amount of time (for example, detection in half the time).

Alternative embodiments wherein the images are overlaid on each other holds potential for substantially increasing the contrast for that species in the composite image, even in the presence of other species that might be detectable at one but not both of the same wavelengths.

According to an aspect of this disclosure, an imaging system is provided with at least one imaging lens or lens assembly and a plurality of spectral filters that rely on polarization alignment. In particular, the spectral filter(s) can comprise one or more tunable filters. The optics can be infinitely corrected or the tunable filters can be disposed at a focal plane. The objective lens collects light from a sample, for example photons scattered, reflected, absorbed, and/or emitted from the sample, and directs the light, for example as a collimated beam, to a tunable filter. Such a filter is inherently sensitive to polarization state. Light emerging from the spectral filter is coupled through the imaging lens to be resolved on an image plane such as a CCD photosensor array.

As discussed above, in a conventional tunable filter configuration, the output beam (i.e., the filtered output from the tunable filter) is limited to one of two orthogonal polarization components of the collected light, which in the case of random polarization is 50% of the light power. However, the configurations of the present disclosure hold potential for increasing the intensity of the image at a photodetector array.

One polarization component of the light from the sample can be transmitted directly through a polarization beam splitter. This component is plane polarized and incident on the tunable filter at the reference alignment of the tunable filter. Therefore, this component is provided at the polarization alignment that obtains a maximum transmission ratio of the passband through the tunable filter.

An alternative embodiment has two orthogonally aligned beam paths and two orthogonally aligned tunable filters. The input light is split into orthogonal beams as above. The two tunable filters are placed along laterally adjacent beam paths. One of the beam paths and tunable filters can operate as already described. The tunable filter on the second beam path can be tuned to the same or a different wavelength. The tunable filter on the second beam path can be oriented parallel to the first tunable filter and preceded by a half wave plate at 45° so as to pre-orient the second beam. Or in another alternative, the half wave plate is omitted and the second tunable filter is physically rotated ±90° from parallel to the first tunable filter. When the tunable filters are tuned to the same wavelengths, the overlaid images are cross-polarized and image intensity at the detector is at the maximum. When the tunable filters are tuned to different wavelengths, the image intensities are at half maximum. However, the dual polarization configuration of the present disclosure holds potential for enhancing the contrast in a resulting image.

Hyperspectral imaging using dual polarization may be implemented to define areas where the probability of finding unknown materials is high. The advantage of using hyperspectral imaging in a scanning mode is its speed of analysis. Raman spectroscopy provides for chemical specificity and may therefore be implemented to interrogate those areas of interest identified by the hyperspectral image. The present disclosure provides for a system and method that combines these two techniques, using the strengths of each, to provide for a novel technique of achieving rapid, reliable, and accurate evaluation of unknown materials. The system and method also hold potential for providing autonomous operation as well as providing considerable flexibility for an operator to tailor searching for specific applications.

The present disclosure contemplates both static and On-the-Move ("OTM") standoff configurations. The present disclosure also contemplates the implementation of the sensor system of the present disclosure onto an Unmanned Ground Vehicle ("UGV"). Integration of these sensors onto small UGV platforms in conjunction with specific laser systems may be configured to achieve a pulsed laser system with a size, weight, and power consumption compatible with small UGV operation. Such a configuration holds potential for implementation in a laser-based OTM explosive location system on a small UGV.

The present disclosure also provides for the application of various algorithms to provide for data analysis and object imaging and tracking. These algorithms may further comprise image-based material detection algorithms, including tools that may determine the size, in addition to identity and location, of unknown materials. Providing this information to an operator may hold potential for determining the magnitude of unknown materials in a wide area surveillance mode. Additionally, algorithms may be applied to provide for sensor fusion. This fusion of Raman and other spectroscopic and/or imaging modalities holds potential for reducing false alarm rates.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

FIGS. 2C and 2D are representative of exemplary packaging options of subsystems of a system of the present disclosure.

FIG. 5A is illustrative of FAST technology.

FIG. 5B is representative of an exemplary packaging option of a FAST device.

DETAILED DESCRIPTION

Reference will now be made in detail to the embodiments of the present disclosure, examples of which are illustrated in the accompanying drawings. Wherever possible, the same reference numbers will be used throughout the drawings to refer to the same or like parts.

Figure 1A:
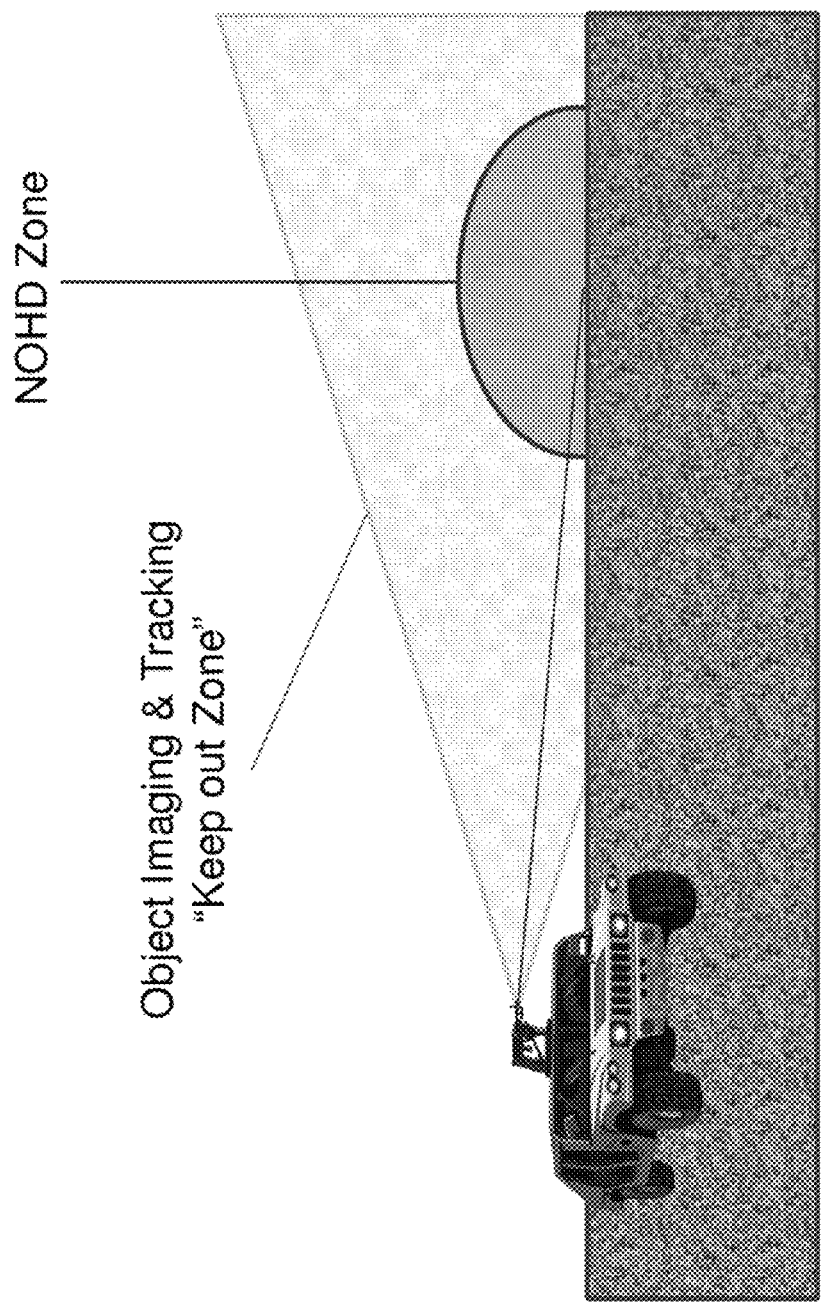
FIGS. 1A and 1B are illustrative of exemplary operational configurations of a system and method of the present disclosure.
Figure 1B:
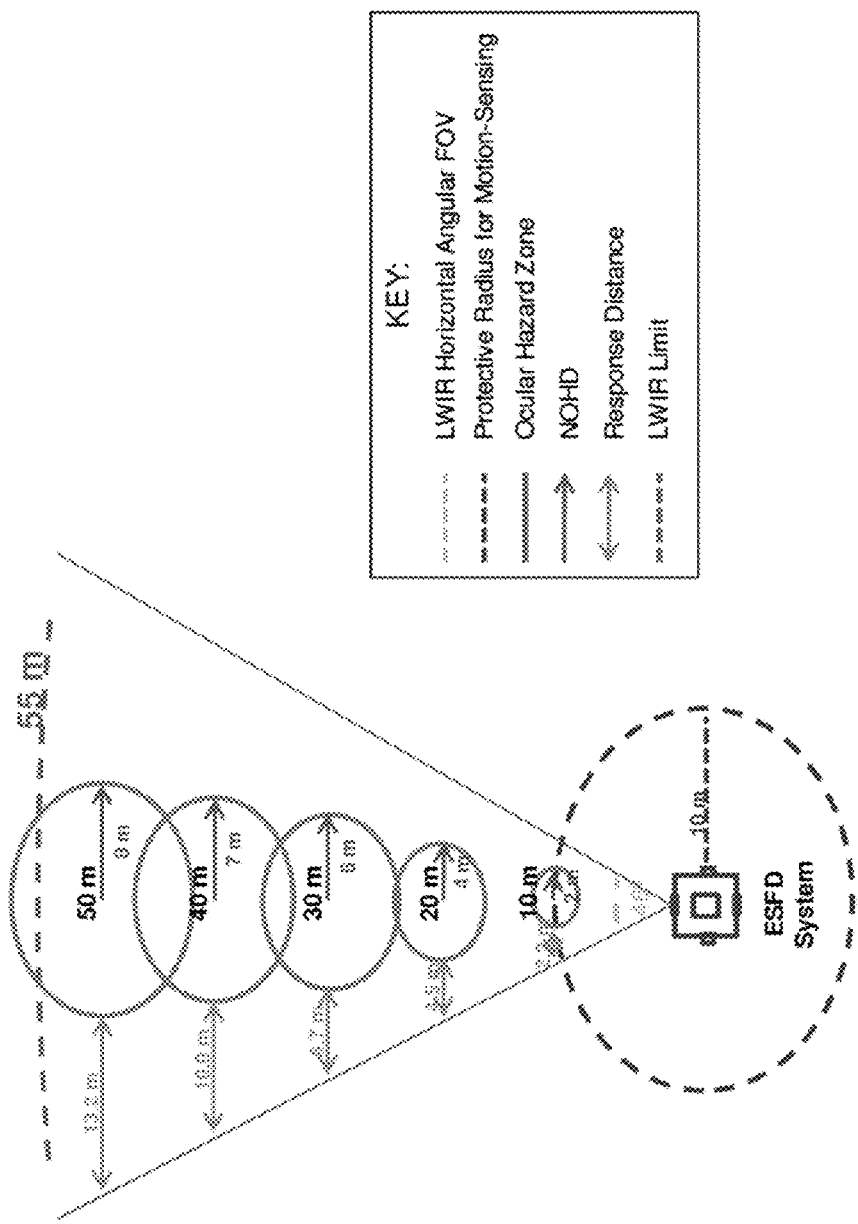

The present disclosure provides for a standoff system for detecting and identifying unknown materials. Examples of operational configurations are illustrated by FIGS. 1A-1B. In one embodiment, the system and method of the present disclosure may be configured to provide for SWIR wide area surveillance of sample scenes. This surveillance may direct the pointing of a Raman sensor by identifying areas of interest comprising potential threats. The present disclosure contemplates a Nominal Ocular Hazard Distance (NOHD) zone protection with human object imaging and a tracking laser kill switch. Specifically, FIG. 1A is illustrative of one CONOPS configuration and FIG. 1B is illustrative of an operational configuration of the present disclosure.

Figures 2A, 2B:
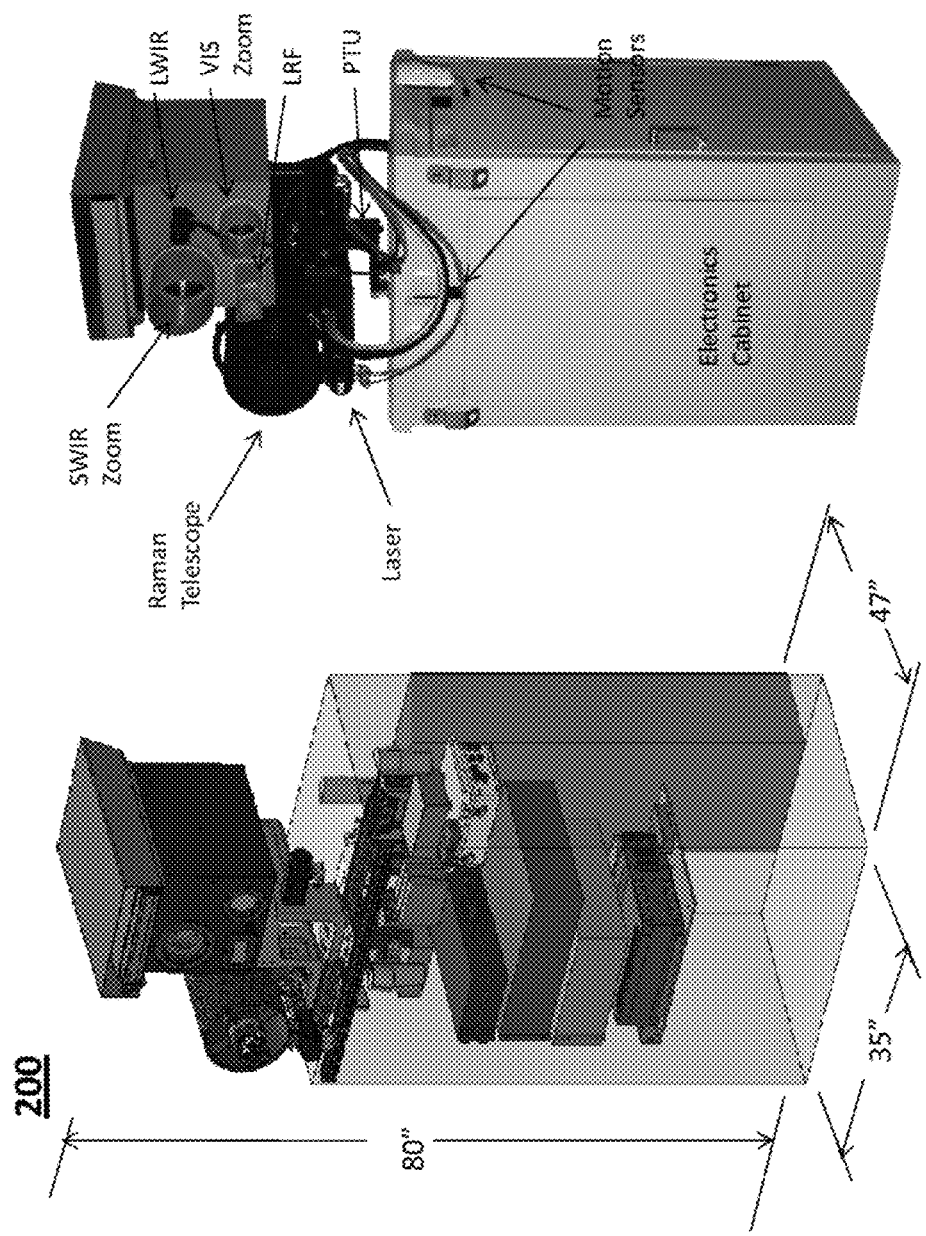
FIGS. 2A and 2B are representative of exemplary packaging options of a system of the present disclosure.

The present disclosure provides for a method for detecting, tracking, and identifying unknown materials. Exemplary housing configurations of a system 200 of the present disclosure are illustrated in FIGS. 2A and 2B. Exemplary configurations of a Raman subsystem 210a and a SWIR subsystem 210b are illustrated in FIGS. 2C and 2D.

Figure 3A:
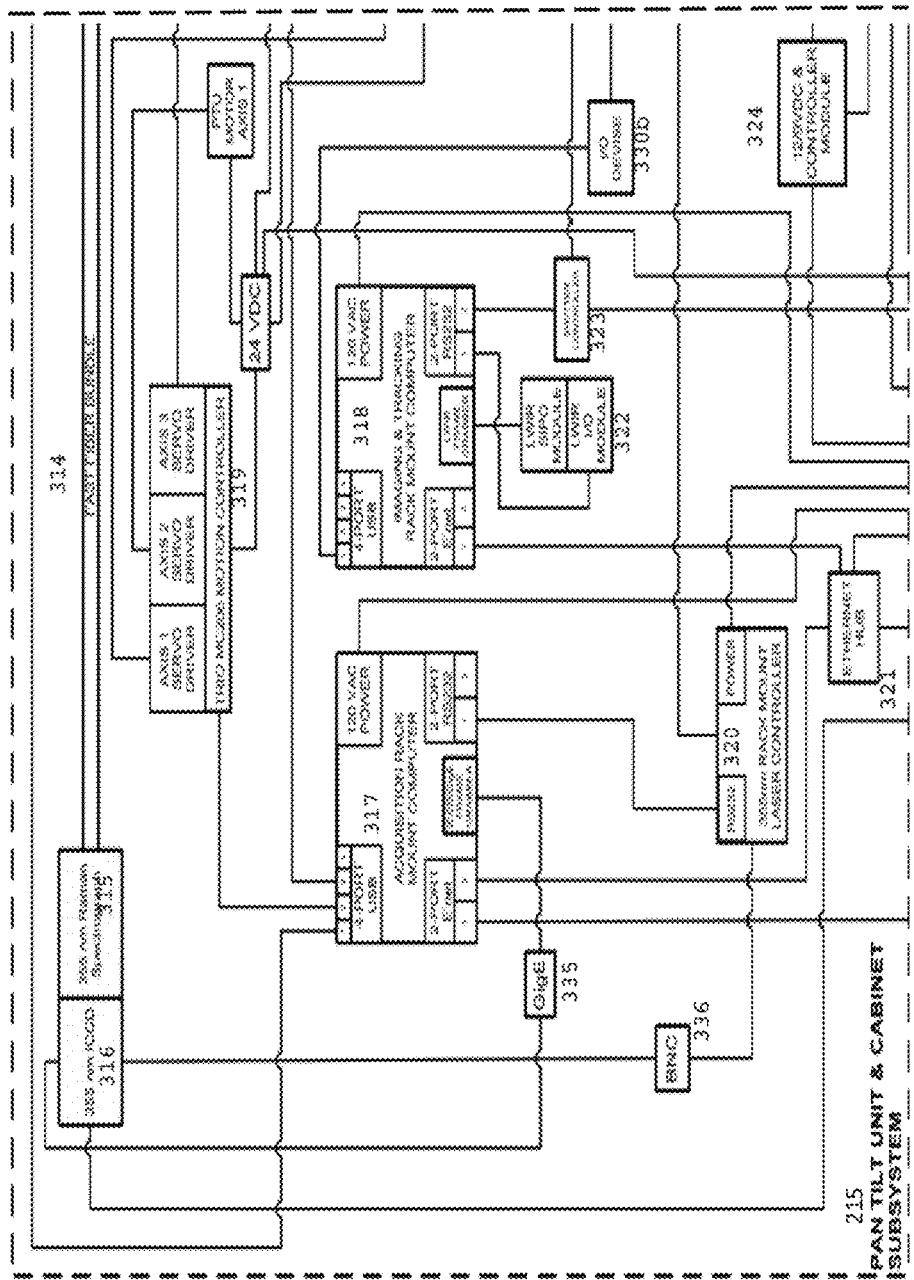
FIG. 3A is representative of a subsystem of a system of the present disclosure.
Figure 3B:
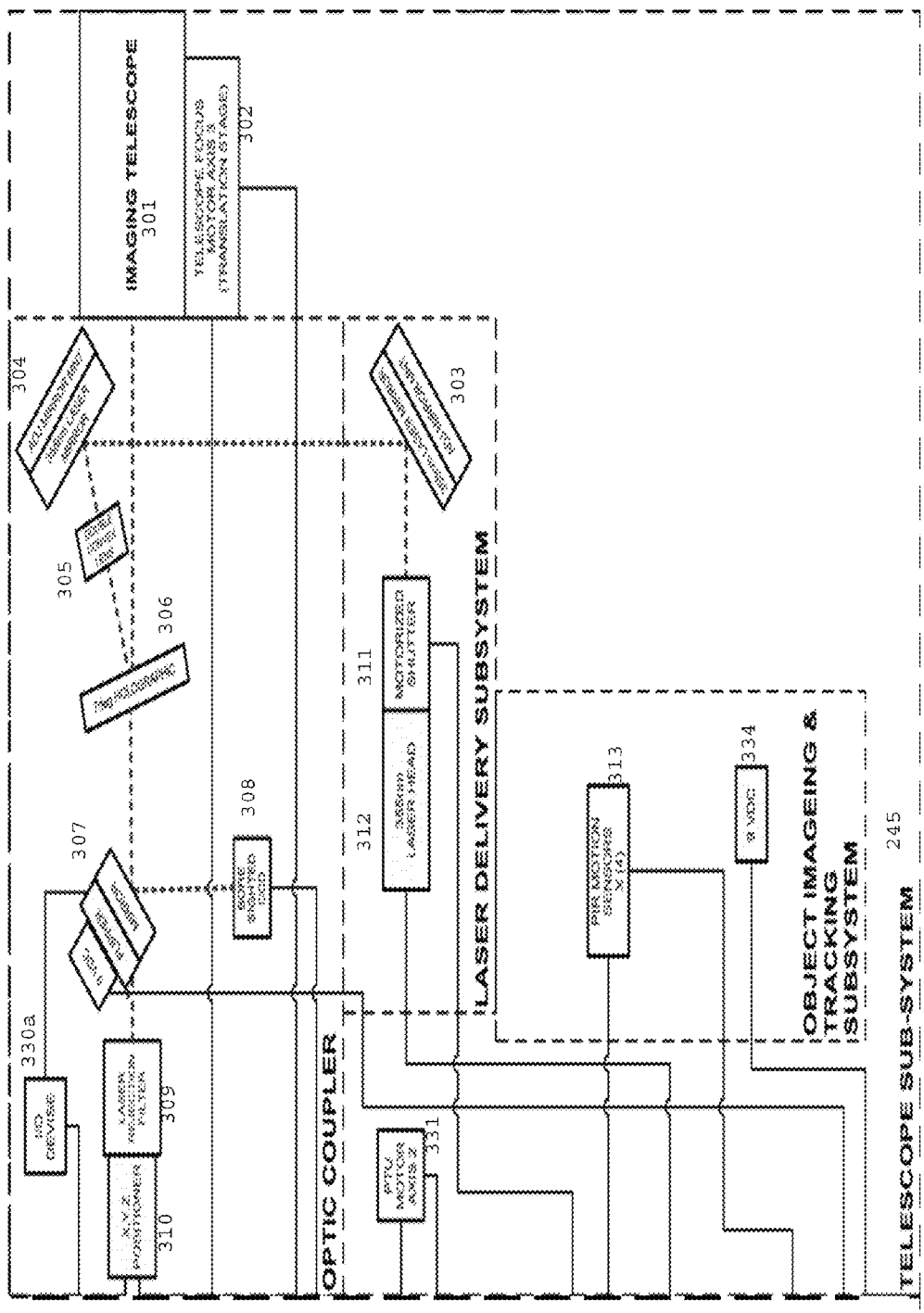
FIG. 3B is representative of a subsystem of a system of the present disclosure.
Figure 3C:
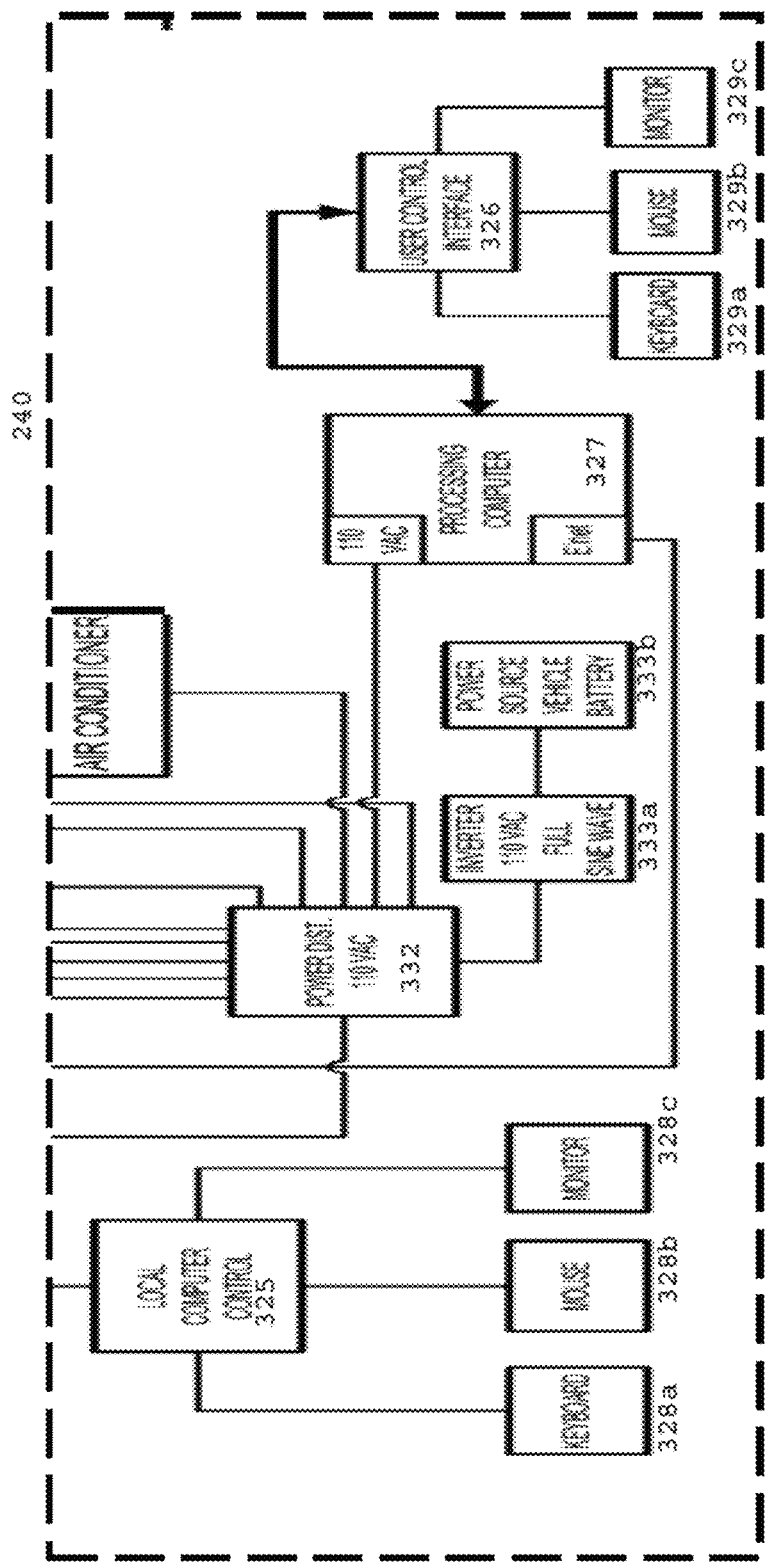
FIG. 3C is representative of a subsystem of a system of the present disclosure.

FIGS. 3A-3C are provided as illustrative embodiments of the subsystems of system 200. The Raman subsystem 210a may comprise a pan tilt unit (PTU) and cabinet subsystem 215, a telescope subsystem 245, a laser delivery subsystem, an optic coupler, an object imaging and tracking subsystem, and power and system processing components.

FIG. 3B is illustrative of a telescope subsystem 245. A telescope subsystem may comprise an imaging telescope 301 and a telescope focus 302. A laser delivery subsystem may comprise a laser head 312 a motorized shutter 311 and mirrors 303. In FIG. 3, leaser head 312 is illustrated as comprising a 355 nm laser. The motorized shutter 311 may be configured so as to effectively stop the illumining photons from a leaser head 312 from illuminating an unknown material.

Illuminating photons may be directed by mirrors 303 to an optic coupler. This optic coupler may comprise mirrors 304, lens 305, and a holographic filter 306 to direct illuminating photons to an imaging telescope 301. In one embodiment, telescope 301 may be replaced with another type of refractive and/or reflective optics (including but not limited to a fixed refractive lens, a variable zoom lens, and others known in the art). These illumination photons may illuminate a second location (region of interest selected for further interrogation after scanning with SWIR hyperspectral imaging) and thereby generate a plurality of interacted photons. These interacted photons may pass through the device and directed by mirror 307 to either a boresighted CCD 308 and/or through a laser rejection filter 309, x,y,z positioned 310 and to a FAST device 314. FAST device and FAST fiber bundle may be used interchangeably herein. The FAST device may be housed in the pan tilt unit and cabinet subsystem 215, illustrated in FIG. 3A.

FAST technology is illustrated in FIG. 5A. FIG. 5B illustrates an exemplary housing configuration of a FAST device. The FAST system can provide faster real-time analysis for rapid detection, classification, identification, and visualization of, for example, explosive materials, hazardous agents, biological warfare agents, chemical warfare agents, and pathogenic microorganisms, as well as non-threatening materials, elements, and compounds. FAST technology can acquire a few to thousands of full spectral range, spatially resolved spectra simultaneously, This may be done by focusing a spectroscopic image onto a two-dimensional array of optical fibers that are drawn into a one-dimensional distal array with, for example, serpentine ordering. The one-dimensional fiber stack is coupled to an imaging spectrograph. Software may be used to extract the spectral/spatial information that is embedded in a single CCD image frame.

One of the fundamental advantages of this method over other spectroscopic methods is speed of analysis. A complete spectroscopic imaging data set can be acquired in the amount of time it takes to generate a single spectrum from a given material. FAST can be implemented with multiple detectors. Color-coded FAST spectroscopic images can be superimposed on other high-spatial resolution gray-scale images to provide significant insight into the morphology and chemistry of the sample.

The FAST system allows for massively parallel acquisition of full-spectral images. A FAST fiber bundle may feed optical information from is two-dimensional non-linear imaging end (which can be in any non-linear configuration, e.g., circular, square, rectangular, etc.) to its one-dimensional linear distal end. The distal end feeds the optical information into associated detector rows. The detector may be a CCD detector having a fixed number of rows with each row having a predetermined number of pixels. For example, in a 1024-width square detector, there will be 1024 pixels (related to, for example, 1024 spectral wavelengths) per each of the 1024 rows.

The construction of the FAST array requires knowledge of the position of each fiber at both the imaging end and the distal end of the array. Each fiber collects light from a fixed position in the two-dimensional array (imaging end) and transmits this light onto a fixed position on the detector (through that fiber's distal end).

Each fiber may span more than one detector row, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

In one embodiment, the system 200 may comprise FAST technology available from ChemImage Corporation, Pittsburgh, Pa. This technology is more fully described in the following U.S. Patents and Published Patent Applications, hereby incorporated by reference in their entireties: U.S. Pat. No. 7,764,371, filed on Feb. 15, 2007, entitled "System And Method For Super Resolution Of A Sample In A Fiber Array Spectral Translator System"; U.S. Pat. No. 7,440,096, filed on Mar. 3, 2006, entitled "Method And Apparatus For Compact Spectrometer For Fiber Array Spectral Translator"; U.S. Pat. No. 7,474,395, filed on Feb. 13, 2007, entitled "System And Method For Image Reconstruction In A Fiber Array Spectral Translator System"; and U.S. Pat. No. 7,480,033, filed on Feb. 9, 2006, entitled "System And Method For The Deposition, Detection And Identification Of Threat Agents Using A Fiber Array Spectral Translator". In one embodiment, the system 200 may comprise FAST technology wherein a fiber stack comprises at least two columns of fibers spatially offset in parallel. This technology is more fully described in U.S. Patent Application Publication No. 2010/0265502, filed on Apr. 13, 2010, entitled "Spatially And Spectrally Parallelized Fiber Array Spectral Translator System And Method Of Use," which is hereby incorporated by reference in its entirety.

Referring again to FIG. 3A, interacted photons may be transferred via a FAST device 314 to a Raman spectrometer 315 and detector to thereby generate at least one Raman data set (such as a plurality of spatially resolved Raman spectra). In FIG. 3A, this detector is illustrated as a ICCD 316.

The PTC and Cabinet subsystem of subsystem 210a may further comprise various computers and controls 317, 318, 320, 321, 324, a motion controller 319, and a PTU motor axis 331 configured for operating the subsystem 210a. An LWIR module 322 may be configured to generate and assess LWIR data to thereby determine human presence in a scene/region of interest. The LWIR module 322 may further comprise at least one refractive or reflective optics, and a LWIR detector configured to generate at least one of: a LWIR hyperspectral image, a spatially accurate wavelength resolved LWIR image, a LWIR spectrum. In one embodiment, the LWIR module 322 may further comprise a tunable filter. The LWIR module 322 may be operatively coupled to a shutter controller 323 to control operation of at least one of: a laser head 312 and motorized shutter 311. I/O devices 330a, 330b and BNC 336 and GigE 335 connections and power sources 332, 333a, 333b, and 334 may also be configured to provide additional power and control.

The subsystem 210a may further comprise an object imaging and tracking subsystem. This object imaging and tracking subsystem may comprise one or more motion sensors 313.

The subsystem 210a may further comprise various components operatively coupled to subsystems to provide control and power sources to the subsystem and its components 240, illustrated in FIG. 3C. These may include a local computer control 325, a user control interface 326, and processing computer 327. Keyboards 328a and 329a, mouse 328b and 329b, and monitors 328c and 329c. Components configured for powering the subsystem 332, 333a, 333b, may also be operatively coupled to the subsystem.

Figure 4A:
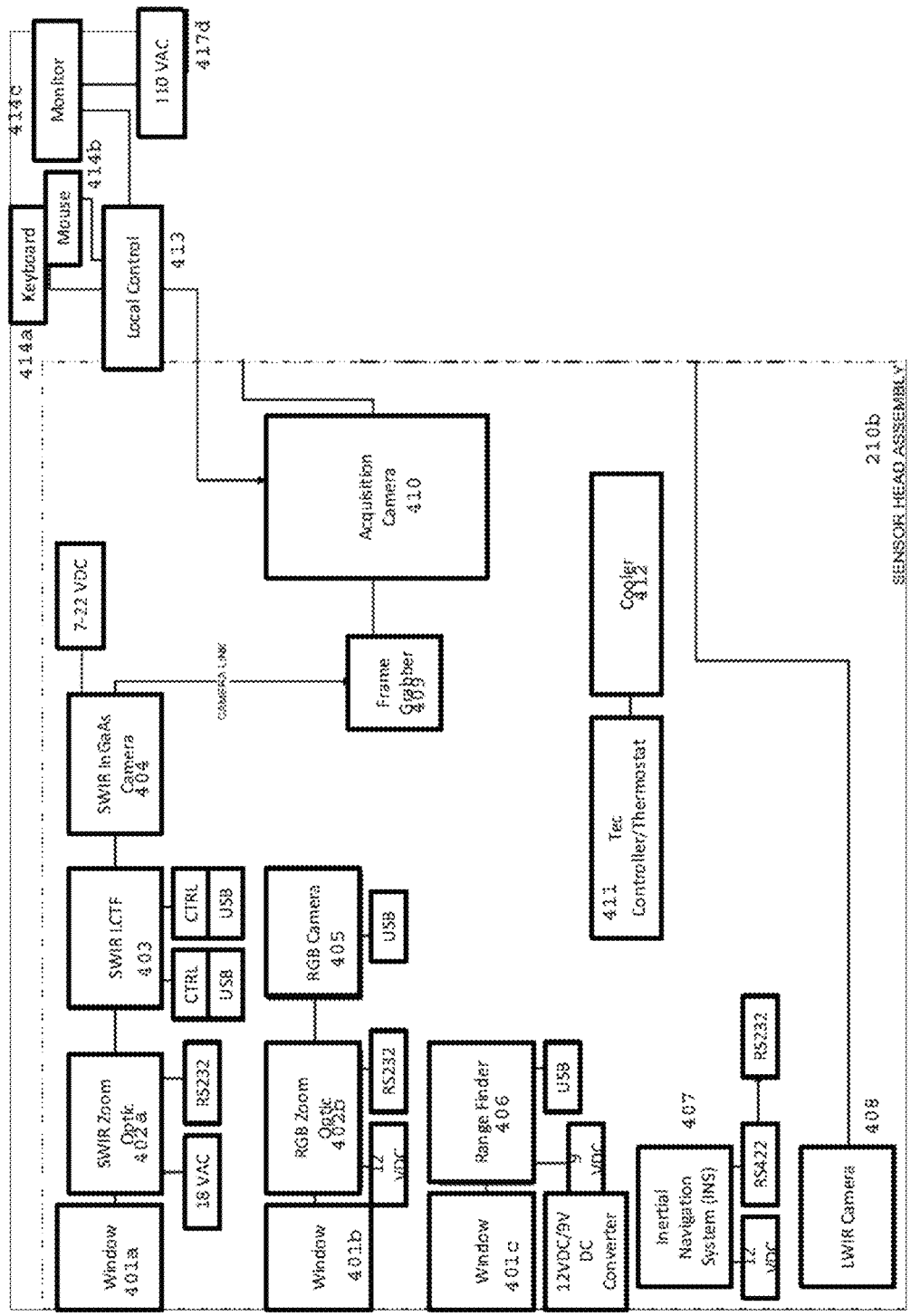
FIG. 4A is representative of a subsystem of a system of the present disclosure.

FIG. 4A is representative of one embodiment of the SWIR subsystem 210b. The subsystem 210b may comprise a sensor head assembly. A sensor head assembly may comprise one or more windows 401a, 401b, and 401c, which may also be referred to as collection lenses, lenses, or collection optics herein. In one embodiment, the collection optics may comprise at least one of: a refractive optic, a reflective optics, and telescope optics. The system may comprise a one or more zoom optics and/or fixed refractive lenses. In one embodiment, a SWIR zoom optic 402a may be operatively coupled to a tunable filter. In FIG. 3, the tunable filter is illustrated as a SWIR liquid crystal tunable filter 403. In another embodiment, the filter may comprise a SWIR multi-conjugate liquid crystal tunable filter. The SWIR liquid crystal tunable filter may 403 may be configured to effectively separate a plurality of interacted photons into a plurality of predetermined wavelength bands. The plurality of interacted photons may be detected by a SWIR detector, illustrated as a SWIR InGaAs Camera 404. However, other embodiments may comprise other detectors known in the art including but not limited to a CCD, an ICCD, an InSb detector, a MCT detector and combinations thereof. In one embodiment a SWIR camera 404 may be operatively coupled to a frame grabber 409.

The sensor head assembly may further comprise a visible zoom optic, illustrated as a RGB zoom optic 402b. This RGB zoom optic 402b may be operatively coupled to visible detector. The visible detector in FIG. 4 is illustrated as an RGB camera 405. However, this visible detector may also comprise a video capture device.

The sensor head assembly of subsystem 210b may further comprise a range finder 406. In one embodiment, at least one of a frame grabber 409, a range finder 406, and an inertial navigation system 407 may be operatively coupled to an acquisition computer 410. This acquisition computer 410 may further, in one embodiment, be coupled to at least one of: a local control 413 and elements housed in a PTU and cabinet subsystem. This PTU cabinet and subsystem may comprise a Ethernet 415 and a processing computer 416. In one embodiment, a local control 413 may comprise at least one of: a keyboard 414a, a mouse 414b, and a monitor 414c. The processing computer 416 may be operatively coupled to a user control interface control 418a. The user control interface system 418a may comprise at least one of: a mouse 418a, keyboard 418b, and monitor 418c.

In one embodiment, the subsystem 210b of the present disclosure may incorporate a high pixel resolution, high frame rate color video camera system to assist in locating materials of interest. The SWIR HSI portion of the system may consist of an InGaAs focal plane camera coupled to a wavelength-agile MCF in combination with a zoom optic capable of viewing a large area, or imaging a localized area at high magnification. In one embodiment of operation, an area would first be screened using the wide field setting on the zoom lens. Once the area is screened and potential materials are identified, confirmation of the area may be accomplished as necessary by using the narrow field setting on the zoom lens.

Another embodiment of the subsystem 210b may further comprise a dual polarization module 420. The present disclosure contemplates at least two different configurations for dual polarization. One utilizes one detector. This embodiment may comprise two independently tunable filters 403a, 403b along distinct orthogonal beam paths for the orthogonal polarization components emerging from a polarizing beamsplitting cube 430a. In one embodiment, the tunable filters may comprise at least one of: a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, a Fabry Perot liquid crystal tunable filter, and combinations thereof. In this arrangement, the paths of the filtered beams are not parallel through the tunable filters 403a, 403b, but are directed by appropriate reflectors (e.g., mirrors) to a SWIR detector 404, at which the orthogonal components, which can be at the same or different passband wavelengths $\omega_1$ and $\omega_2$. In one embodiment, the components may be combined at a second polarizing beamsplitting cube 430b and directed to the detector 404. In another embodiment, the components may be kept separate as they are directed to the detector 404. However, the beam paths from one beam splitter 430a to the other 430b (via individual tunable filters 403a, 403b) may be made symmetrical to avoid, for example, need for infinitely-corrected optics. In FIG. 4A, the detector 404 may comprise other detectors including but not limited to: a CCD, CMOS, an InGaAs, a PtSi, InSb, a HgCdTe detector, and combinations thereof.

The two tunable filters 403a, 403b may be tuned in unison to the same wavelengths ($\omega_1 = \omega_2$) using a tunable filter controller (not illustrated). It is possible to configure the controller to independently tune the passband wavelengths $\omega_1$ and $\omega_2$ of the tunable filters 403a, 403b that respectively process orthogonal components of the input. Therefore, by appropriate control, the tunable filters can be tuned to the same wavelength or to two different passband wavelengths ($\omega_1 \neq \omega_2$) at the same time. The controller may be programmable or implemented in software to allow a user to selectively tune each tunable filter 403a, 403b as desired.

Figure 4B:
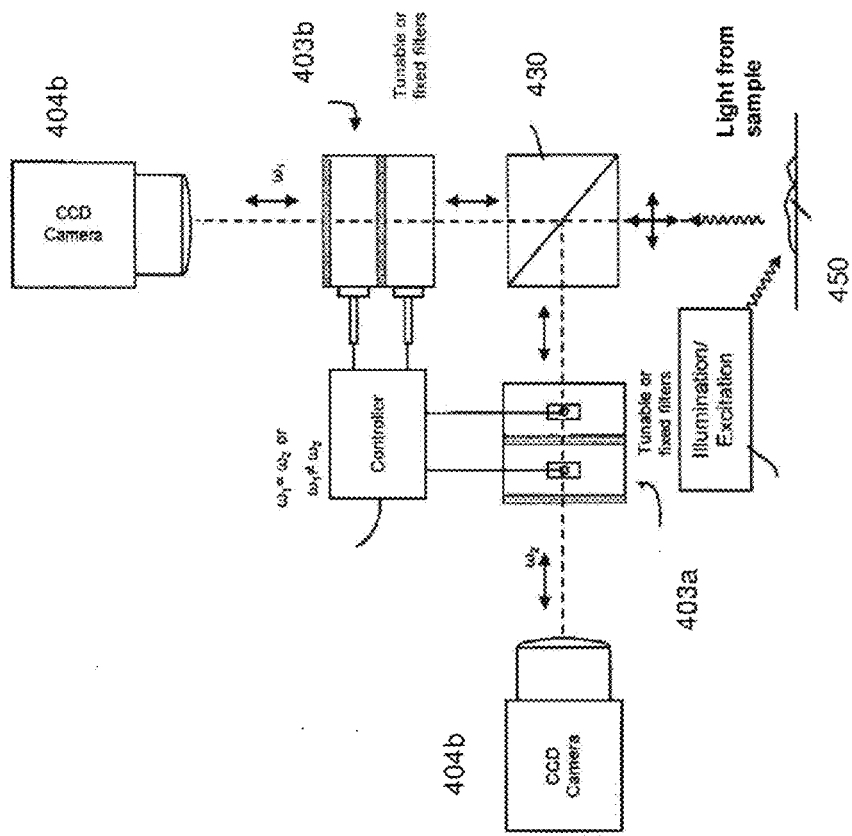
FIG. 4B is representative of a subsystem of a system of the present disclosure comprising dual polarization.

A fast switching mechanism may be provided to switch between the two views (or spectral images) corresponding to spectral data collected by the detector 404 from each of the tunable filter 430a, 430b. Alternatively, such two spectral views or images (from two separate tunable filters) may be combined or overlaid into a single image, for example, to increase contrast or intensity or for comparison purposes. This embodiment may include a single CCD detector 404 to capture the filtered signals received from the tunable filters 430a, 430b. In another embodiment, polarizing beamsplitting cube 430b may be removed and two detectors cameras may be used. An exemplary embodiment of such a configuration is illustrated in FIG. 4B. Each detector 404a and 404b may be optically coupled to a corresponding one of the two tunable filters 403a, 403b to capture filtered signals from the tunable filters and to responsively generate electronic signals that enable display of spectral images of the illuminated sample 450. The present disclosure contemplates that any number of optical filters and associated detectors may be used to achieve the benefit of dual polarization as described herein.

In one embodiment, the two filtered signals may be detected simultaneously. As discussed herein, simultaneous detection of two different wavelengths holds potential for real-time detection when displayed in a non-overlapping configuration (side-by-side, top to bottom, etc.). In another embodiment, the two filtered signals may be detected sequentially.

It is noted here that although laser light may be coherent, the light received from the sample 450 (e.g., light emitted, scattered, absorbed, and/or reflected) and fed to the tunable filters 403a, 403b may not be coherent. Therefore, wavefront errors may not be present or may be substantially avoided in the two tunable filters version in FIG. 4B because of processing of non-coherent light by each tunable filter 403a, 403b.

The present disclosure also provides for a method for analyzing a sample comprising an unknown material. The method may comprise collecting a first plurality of interacted photons from a first location comprising at least one unknown material. The first plurality of interacted photons may comprise optical components in a plurality of polarization alignments. The first plurality of interacted photons may be separated into a first optical component and a second optical component. The first optical component may be transmitted with a first polarization alignment and the second optical component may be transmitted with a second polarization alignment.

The first optical component may be passed through a first optical filter configured to transmit at least a portion of the first optical component having a first wavelength and the second optical component may be passed through a second optical filter configured to transmit at least a portion of the second optical component having a second wavelength.

The first optical component and the second optical component may be detected and at least one SWIR data set may be generated representative of the first location. The SWIR data set may comprise at least one of: a SWIR hyperspectral image, a SWIR spectra, and a SWIR spatially accurate wavelength resolved image. In one embodiment, the SWIR data sets may be overlaid on a detector. In another embodiment, the SWIR data sets may be displayed in a manner other than overlaid. The SWIR data set(s) may be analyzed to identify a second location comprising the unknown material. In one embodiment, the SWIR data set(s) may be analyzed by comparison with at least one reference data set associated with a known material. This analysis may target one or more areas of interest. These may be areas of the first location likely to comprise the unknown material (or a specific material of interest).

These second location(s) may be illuminated to generate a second plurality of interacted photons using a laser illumination source. In one embodiment, the second plurality of interacted photons may comprise at least one of: photons scattered by the sample, photons reflected by the sample, photons emitted by the sample, and photons absorbed by the sample. The second plurality of interacted photons may be passed through a fiber array spectral translator device and detected to generate at least one Raman data set representative of the second location. In one embodiment, the Raman data set may comprise a plurality of spatially resolved Raman spectra. However, the present disclosure also provides for the Raman data set comprising at least one of: a hyperspectral image and a spatially resolved Raman image. The Raman data set may be analyzed to associate the unknown material with a known material. This analysis may further comprise comparing the Raman data set with at least one reference data set associated with a known material.

In one embodiment, the method may further comprise applying at least one of an object detection algorithm, an object tracking algorithm, and combinations thereof. In one embodiment, the present disclosure provides for object detection. This may include application of motion detection techniques to find moving objects. Adaptive threshold algorithms may be used to vary detection thresholds with the content of a scene. ROIs positions and geometric and/or statistical properties may be extracted and fed into a tracker.

In one embodiment, the present disclosure provides for Bayesian track classification. A Bayesian classifier may encode important features of the objects to be classified. In one embodiment, four classification features may be employed. Lookup tables may be generated in an offline training process. Two class estimates (i.e., "probability of a human" vs. "probability not a human") may be computed from lookup tables and from the features computed at runtime. If at least one track is declared to be class "human" in a single frame then the shutter may be closed.

In one embodiment, the method may further comprise obtaining and analyzing at least one LWIR data set from a third location substantially simultaneously with the SWIR hyperspectral detection. This LWIR data set may comprise at least one of: a hyperspectral image, a spatially accurate wavelength resolved image, and a LWIR spectra. The LWIR data set may be analyzed to determine at least one of: the presence of at least one human in said region of interest and the absence of a human in said region of interest. If at least one human is detected, the illumination may be stopped. This may be achieved by activating a laser shutter. In one embodiment, at least a portion of the first location (analyzed using SWIR hyperspectral imaging, the second location (analyzed using Raman spectroscopy), and a third location (analyzing using at least one of LWIR imaging and motion detectors) at least partially overlap. In one embodiment, the first location and the third location are substantially the same (scanning substantially the same wide field area) and the second location(s) are within the first and third locations (further interrogation of region(s) of interest within a scene).

In one embodiment, a method may further comprise providing a reference database comprising at least one reference data set, wherein each reference data set is associated with a known material. SWIR, LWIR, and/or Raman data sets obtained from interrogation of unknown materials during testing may be compared to at least one reference data set. This comparison may be used to identify regions of interest of a sample scene likely to comprise materials of interest or to identify unknown materials.

In one embodiment, this comparison may be achieved by applying one or more chemometric techniques. This chemometric technique may be selected from the group consisting of: principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, Bayesian fusion, and combinations thereof.

In one embodiment, a method may further comprise outputting a video image and/or RGB image representative of a sample scene, a region of interest within said sample scene, and combinations thereof. This image may be used to aid in surveillance and detection.

Figure 6:
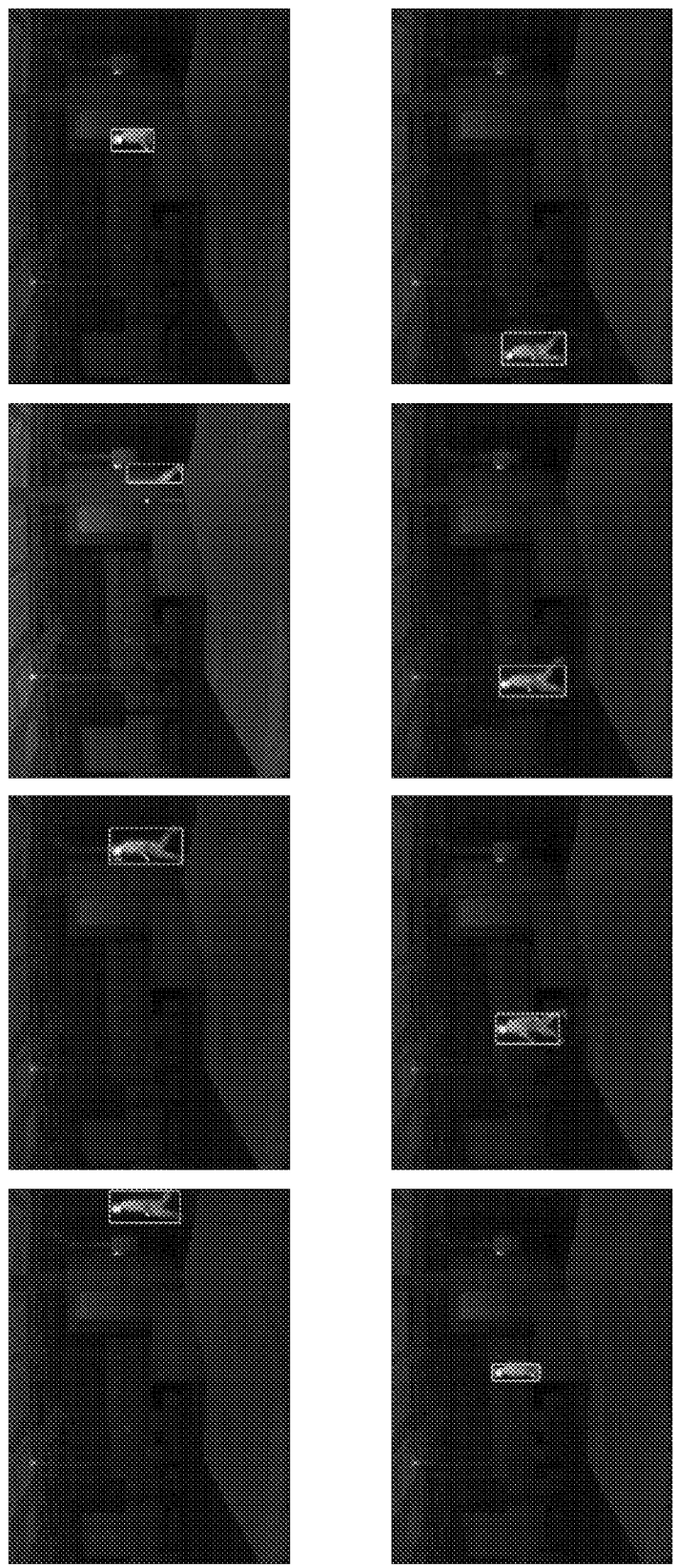
FIG. 6 is illustrative of the tracking capabilities of the present disclosure.
Figure 7:
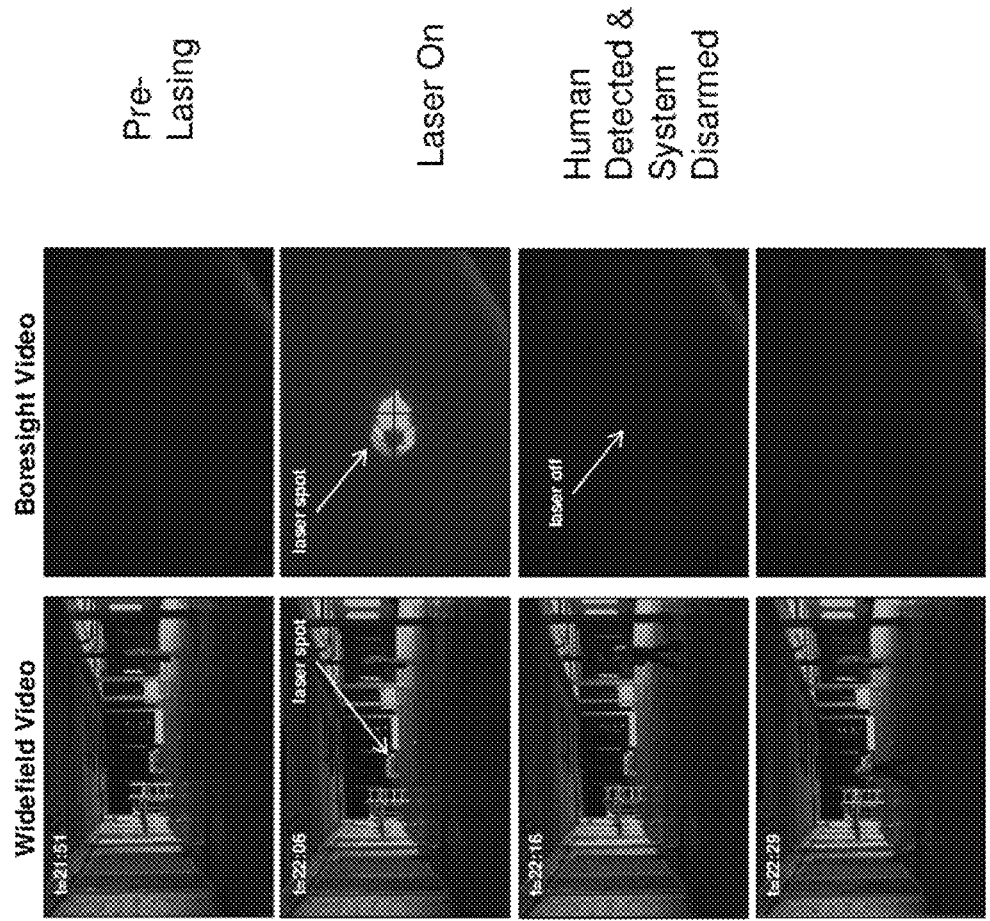
FIG. 7 is illustrative of the tracking capabilities of the present disclosure.
Figure 8A:
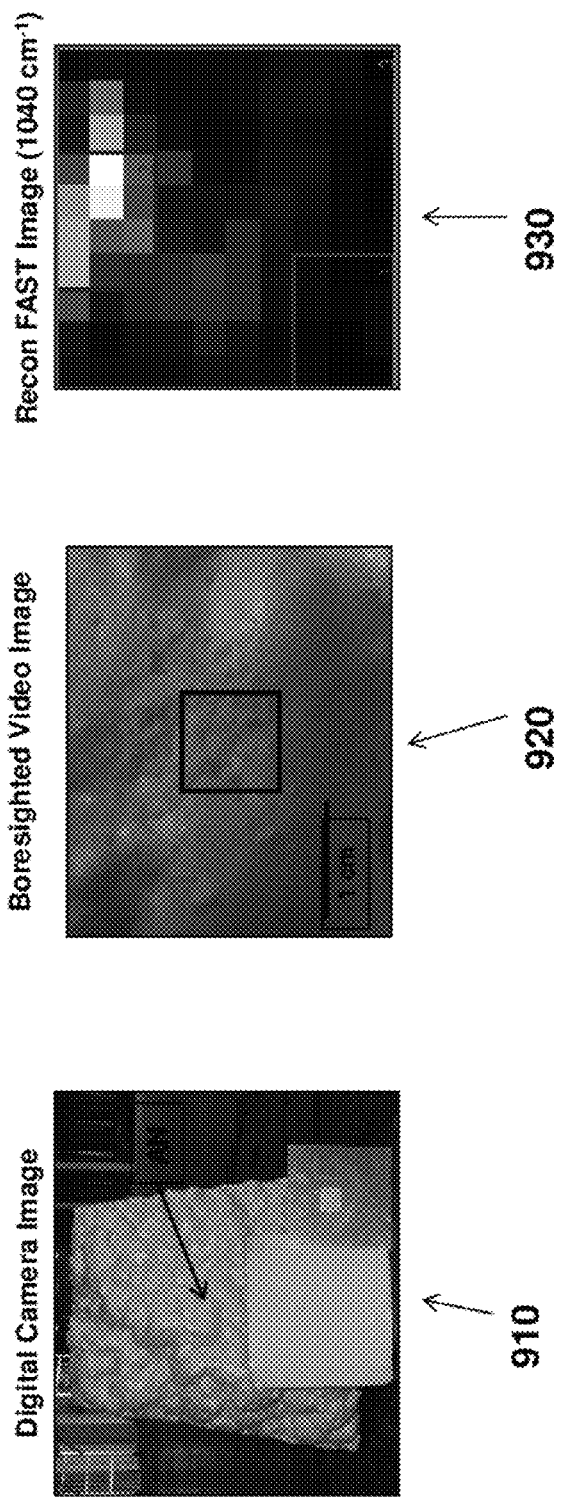
FIG. 8A is representative of detection capabilities of the present disclosure.
Figure 8B:
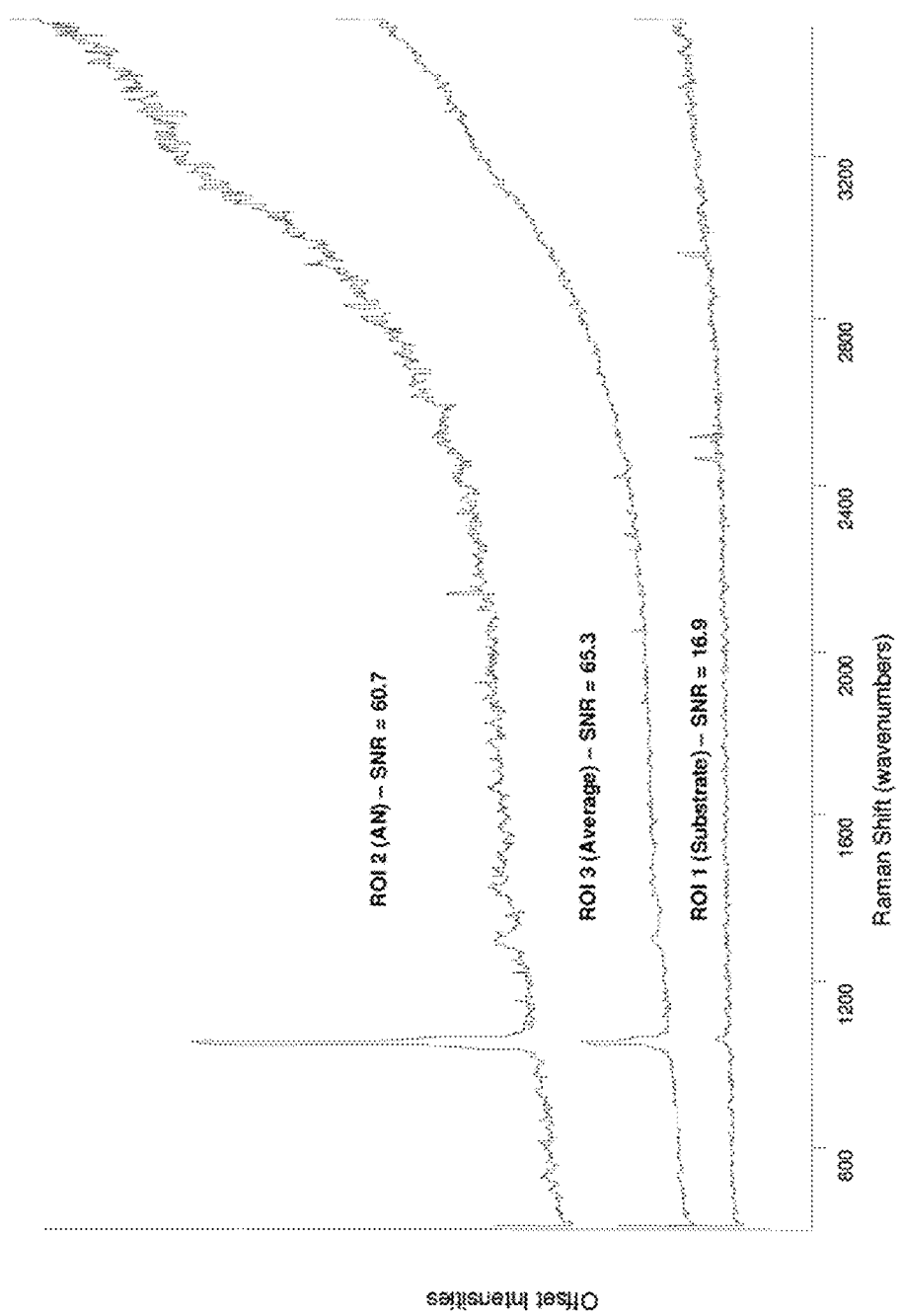
FIG. 8B is representative of detection capabilities of the present disclosure.

FIGS. 6 and 7 are illustrative of human detection capabilities of the present discourse using LWIR data. As can be seen from these figures, a human can be detected and a system disarmed based on this presence. FIGS. 8A and 8B are illustrative of the detection capabilities of the present disclosure. FIGS. 8A and 8B illustrate the ability of the system and method disclosed herein to detect explosive material on a surface. A digital camera image 910 illustrates a sample scene, 920 represents a boresighted video image with a region of interest outlined in green. A FAST image is illustrated in 930. Spectra associated with regions of interest in FIG. 8A are illustrated in FIG. 8B.

The present disclosure may be embodied in other specific forms without departing from the spirit or essential attributes of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A system comprising:
   a first subsystem comprising:
      a first collection optics configured to collect a first plurality of interacted photons from a first location comprising at least one unknown material, wherein the first plurality of interacted photons comprise optical components in a plurality of polarization alignments,
      a first polarization assembly configured to:
         receive the first plurality of interacted photons,
         separate the first plurality of interacted photons into a first optical component and a second optical component, and
         transmit the first optical component with a first polarization alignment and the second optical component with a second polarization alignment,
      a first optical filter configured to receive the second optical component and transmit at least a portion of the second optical component having a first wavelength,
      a second optical filter configured to receive the second optical component and transmit at least a portion of the second optical component having a second wavelength,
      at least one short wave infrared detector configured to detect at least one of the first optical component and the second optical component and generate a SWIR data set representative of the first location;
   a second subsystem comprising:
      an illumination source configured to illuminate a second location comprising at least one unknown material to generate a second plurality of interacted photons,
      a second collection optics configured to collect the second plurality of interacted photons,
      a fiber array spectral translator device, wherein the device further comprises a two-dimensional array of optical fibers drawn into a one-dimensional fiber stack so as to effectively convert a two-dimensional field of view into a curvilinear field of view, and wherein the two dimensional array of optical fibers is configured to receive a plurality of photons and transfer the photons out of the fiber array spectral translator device,
      a spectrometer comprising an entrance slit coupled to the one-dimensional end of the fiber stack, wherein the spectrometer is configured to generate a plurality of Raman spectra, and
      a Raman detector configured to detect the photons from the spectrometer and generate a Raman data set representative of the second location;
   a third subsystem comprising:
      a third collection optics configured to collect a third plurality of interacted photons from a third location,
      a long wave infrared detector configured to detect the third plurality of interacted photons and generate a LWIR data set representative of the third location.

2. The system of claim 1 wherein the first subsystem further comprises a RGB camera configured to generate a RGB video image of at least one of the first location, the second location, and the third location.

3. The system of claim 1 wherein at least one of the first optical filter and the second optical filter further comprise a tunable filter.

4. The system of claim 3 wherein the tunable filter further comprises at least one of: a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, and a Fabry Perot liquid crystal tunable filter.

5. The system of claim 1 wherein at least one SWIR detector further comprises a focal plane array.

6. The system of claim 5 wherein the focal plane array further comprises at least one of: a InGaAs detector, a CMOS detector, an InSb detector, a MCT detector, an ICCD detector, and a CCD detector.

7. The system of claim 1 wherein a first SWIR detector is configured to detect the first optical component, further comprising a second SWIR detector configured to detect a second optical component.

8. The system of claim 1 wherein at least one of the first collection optics, the second collection optics, and the third collection optics further comprise a telescope optics.

9. The system of claim 1 wherein the Raman detector further comprises a focal plane array.

10. The system of claim 9 wherein the focal plane array further comprises at least one of: a InGaAs detector, a CMOS detector, an InSb detector, a MCT detector, an ICCD detector, and a CCD detector.

11. The system of claim 1 wherein the LWIR detector further compromises a focal plane array.

12. The system of claim 11 wherein the focal plane array further comprises at least one of: a InGaAs detector, a CMOS detector, an InSb detector, a MCT detector, an ICCD detector, and a CCD detector.

13. The system of claim 1 further comprising a third optical filter configured to filter the third plurality of interacted photons into a plurality of wavelength bands.

14. The system of claim 1 further comprising a shutter coupled to the illumination source.

15. The system of claim 1 further comprising at least one reference database comprising at least one reference data set, wherein each reference data set is associated with a known material.

16. The system of claim 1 further comprising a processor configured to analyze at least one of the SWIR data set and the Raman data set.

17. The system of claim 1 wherein at least one of the first optics, the second optics, and the third optics further comprises at least one of: a refractive optic and a reflective optic.

18. A method comprising:
surveying a first location comprising at least one unknown material, wherein surveying comprises:
collecting a first plurality of interacted photons from a first location comprising at least one unknown material, wherein the first plurality of interacted photons comprise optical components in a plurality of polarization alignments,
separating the interacted photons into a first optical component and a second optical component,
transmitting the first optical component to a first optical filter and the second optical component to a second optical filter,
passing the first optical the first optical component through a first optical filter configured to transmit at least a portion of the first optical component having a first wavelength,
passing the second optical component through a second optical filter configured to transmit at least a portion of the second optical component having a second wavelength, and
detecting the first optical component and the second optical component using at least one short wave infrared detector to generate at least a first SWIR data set representative of the first location and a second SWIR data set representative of the first location,
analyzing at least one of the first SWIR data set and the second SWIR data set to identify a second location comprising the unknown material;
targeting the second location, wherein targeting comprises:
illuminating the second location to generate a second plurality of interacted photons using a laser illumination source;
passing the second plurality of interacted photons through a fiber array spectral translator device, and
detecting the second plurality of interacted photons and generating at least one Raman data set representative of the second location, and
analyzing the Raman data set to thereby associate the unknown material with a known material.

19. The method of claim 18 further comprising
collecting a third plurality of interacted photons from a third location comprising the unknown material;
generating at least one LWIR data set representative of a third location; and
analyzing the LWIR data set to determine at least one of: the presence of a human in the third location and the absence of a human in the third location.

20. The method of claim 19 wherein if the presence of a human is detected in the third location, further comprising stopping laser illumination.

21. The method of claim 19 wherein analyzing the LWIR data set further comprise comparing the data set with at least one reference data set wherein each reference data set is associated with a known material.

22. The method of claim 19 further comprising generating a RGB image of the third location.

23. The method of claim 19 wherein at least a portion of the first location, the second location, and the third location overlap.

24. The method of claim 19 wherein the LWIR data set further comprises a hyperspectral image.

25. The method of claim 19 wherein the LWIR data set further comprises at least one of: a LWIR spectrum and a spatially accurate wavelength resolved LWIR image.

26. The method of claim 18 wherein the first optical component and the second optical component are detected simultaneously.

27. The method of claim 18 wherein the first optical component and the second optical component are detected sequentially.

28. The method of claim 18 wherein the first SWIR data set and the second SWIR data set are displayed in an overlaid configuration.

29. The method of claim 18 wherein the first SWIR data set and the second SWIR data set are displayed in a non-overlaid configuration.

30. The method of claim 18 wherein analyzing at least one of the SWIR data set and the Raman data set is achieved by comparing the data set with at least one reference data set, wherein each reference data set is associated with a known material.

31. The method of claim 30 wherein the comparison is achieved by applying at least one chemometric technique.

32. The method of claim 18 further comprising generating a RGB image of at least one of: the first location and the second location.

33. The method of claim 18 wherein at least a portion of the first location and the second location overlap.

34. The method of claim 18 wherein the SWIR data set further comprises a hyperspectral image.

35. The method of claim 18 wherein the SWIR data set further comprises at least one of: a SWIR spectrum and a spatially accurate wavelength resolved SWIR image.

36. The method of claim 18 wherein the Raman data set further comprises a plurality of spatially resolved Raman spectra.

* * * * *